US006569415B1

(12) United States Patent
Orloff et al.

(10) Patent No.: US 6,569,415 B1
(45) Date of Patent: May 27, 2003

(54) INDICATING SHAVING PREPARATIONS

(75) Inventors: Glennis J. Orloff, Woodbridge, CT (US); Michael C. Dooling, Middlebury, CT (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/628,123

(22) Filed: Jul. 28, 2000

(51) Int. Cl.[7] ................................................. A61K 7/15
(52) U.S. Cl. ........................................................ 424/73
(58) Field of Search ............................................ 424/73

(56) References Cited

U.S. PATENT DOCUMENTS

| | | | | |
|---|---|---|---|---|
| 4,439,416 A | * | 3/1984 | Cordon et al. ................ 424/47 |
| 4,960,585 A | * | 10/1990 | Tehrani ...................... 424/7.1 |
| 5,026,542 A | * | 6/1991 | Baines et al. .................. 424/73 |
| 5,334,325 A | * | 8/1994 | Chaussee ............... 252/174.16 |
| 5,378,468 A | * | 1/1995 | Suffis et al. ................ 424/401 |
| 5,560,859 A | * | 10/1996 | Hartmann et al. ........... 510/135 |

\* cited by examiner

*Primary Examiner*—James M. Spear
(74) *Attorney, Agent, or Firm*—Peter C. Richardson; Gregg C. Benson; Raymond D. Thompson

(57) ABSTRACT

A shaving preparation that undergoes a change discernible to the user when the hair to be shaved has had time to absorb water and soften, when the shaving preparation has been sufficiently hydrated, after a period of time in which proper hair hydration would normally be expected to have been achieved, or any combinations thereof. Shaving preparations of this type advantageously alert the user when at least one desired shaving condition exists.

79 Claims, 1 Drawing Sheet

INDICATING SHAVING PREPARATIONS

The present invention is related to shaving preparations and, more particularly, to shaving preparations comprising an indicator to alert the user when one or more shaving conditions exist.

BACKGROUND

The present invention relates to wet shaving. Those skilled in the art appreciate that certain conditions, such as proper hydration of the hair prior to removal, are important in order to attain an optimum shave. Often shavers apply shaving preparations such as foams, creams, or gels to the area being shaved, such as the face for men, and then immediately begin to remove the hair with a wet razor resulting in a less than optimum shave. In order to obtain an optimal wet shave, it is desired to hydrate the hairs by applying water to the area followed by a shaving preparation that remains on the hair for a certain amount of time, for example a minute or more, before beginning to shave. This provides the hairs with time to absorb the moisture and to consequently soften.

Previously known shaving products and preparations do not provide any indication to the user of when proper shaving conditions exist. It would therefore be desirable to provide shaving products and preparations that provide some discernible indication to their users that optimal shaving conditions exist.

SUMMARY OF THE INVENTION

One aspect of the present invention comprises a shaving preparation that changes color when the hair has had time to absorb water and soften. Shaving preparations of this type advantageously alert the user when the desired shaving conditions exist. A color change of the shaving preparation, or portions thereof, can also be utilized to alert the user when the shaving preparation is properly applied in tandem with water.

According to another aspect of the present invention other indicators such as temperature and scent can be used to alert the user when one or more of the proper shaving conditions exist. For example, the sensation of heat can be used alone to indicate that the hair has had time to absorb water and soften as well as to alert the user when the shaving preparation is properly applied in tandem with water. Heat can also be used in conjunction with a color indication. For example, the shaving preparation can generate an increase in temperature when water is used properly with the shaving preparation and then change color after enough time has elapsed to hydrate the hairs. Similarly, scents can be emitted from the shaving preparation to provide an indication that the shaving preparation is being applied with water and that enough time has elapsed for the hairs to hydrate and soften.

DETAILED DESCRIPTION

Figure 1:
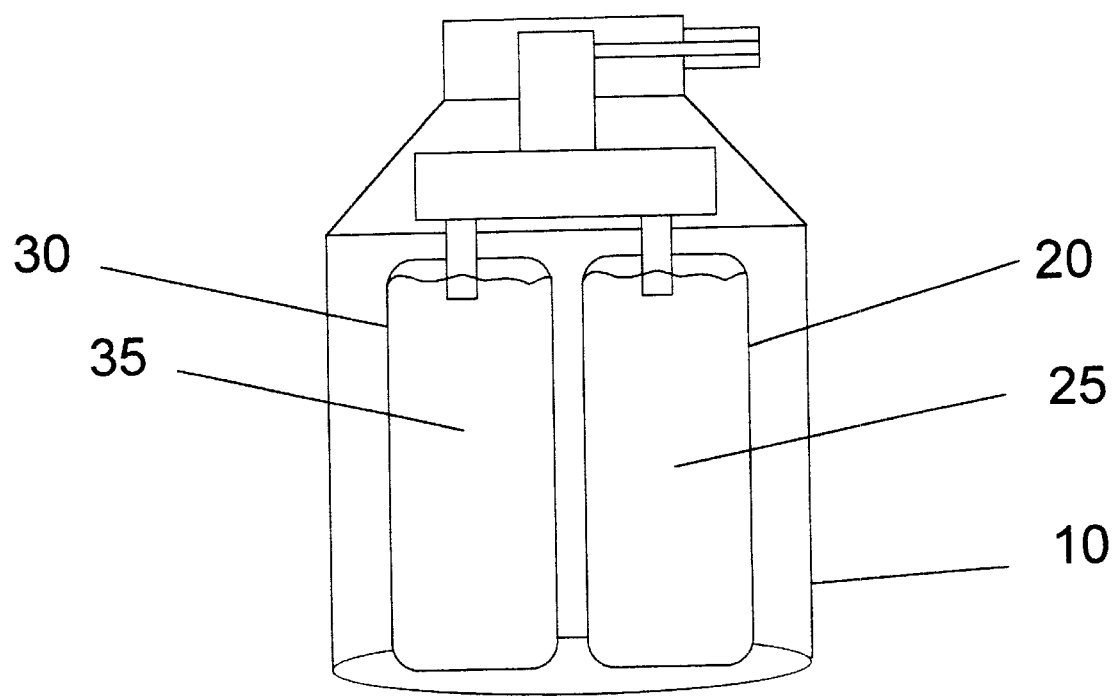
FIG. 1 illustrates one dispenser used for with one embodiment of the present invention.

The various aspects of the present invention are designed to provide shaving preparations that provide discernable indicia to their users of pre-determined shaving conditions. For example, one preferred aspect of the present invention provides at least one visual indication of proper hair hydration, proper hydration of the shaving preparation, a period of time in which proper hair hydration would normally be expected to have been achieved, or any combination thereof. The various aspects of the present invention are designed to enhance the quality of the shave received by avoiding shaving under less than optimal conditions, such as the commonly occurring premature commencement of shaving prior to proper hydration of the hair being shaved.

One of the preferred embodiments of the present invention comprises shaving preparations with color changing chemistry. According to this preferred embodiment, when the shaving preparation has been applied to the area being shaved and/or a sufficient amount of water has been intermixed with the shaving preparation, a chemical reaction is initiated. This chemical reaction requires a certain amount of time and results in a discernible change to the color of at least portions of the shaving preparation. The time for the reaction is advantageously at least as long as is normally required for the hydrated shaving preparation to sufficiently hydrate and soften the hairs to allow an optimum shave. The term "color changing chemistries" is meant to include, but is not limited to, oxidation, hydration, and acid-base reactions. As used herein, the terms "color changing chemistries" or "chemical reactions" do not include physical changes of a shaving preparation resulting purely from aeration. Oxidation reactions are readily initiated once the product is exposed to the atmosphere. Several types of leuco dyes produce colored by-products when oxidized. Another approach to oxidation reactions is to reduce common FDA approved colorants prior to incorporation into the shaving preparation formulation. When these reduced colorants are exposed to the atmosphere they react with the oxygen thus returning the dye to its original color. Reaction rates for such oxidation reactions can be adjusted by encapsulating the dye or synthesizing protective groups onto the dye. Oxidation, hydration, or acid-base reactions can activate the encapsulant. Another suitable approach includes encapsulating standard dyes of desired color that generate a color once released. Compound release rates depend on the rate of capsule degradation. Hydration and acid-base reactions in which water or a pH change is used to initiate the color change are also suitable. Many shaving preparations are basic and when water is properly applied prior to the shaving preparation, the pH can drop to a more neutral pH. Common pH indicator dyes such as rosolic acid, cresol red, and phenol red naturally change color in the desired pH range. Timing of the color change can also be adjusted by encapsulating the indicator or synthesizing protective groups onto the indicator to slow down the reaction rate.

According to another aspect of the present invention other indicators such as temperature and scent can be used to alert the user when one or more desired shaving conditions exist. Temperature changes can result from simple exothermic or endothermic chemical reactions. Specifically, an exothermic hydration reaction would generate enough heat that would be noticeable to the user and the rate can be adjusted by the use of encapsulant or protective groups on one of the reactants. Heat can also be used in conjunction with a color indication. For example, the shaving preparation can generate an increase in temperature when water is used properly with the shaving preparation via an exothermic hydration reaction, e.g. zeolite and water reactions, and then change color after enough time has elapsed to hydrate the hairs using one of the chemistries previously discussed. A plurality of sequential color changes can also be utilized in accordance with the present invention. For example, a plurality of leuco dyes, preferably at least one of which has been chemically modified, can be used to sequentially indicate that a sufficient amount of water has been mixed with the shaving preparation by a first color change, e.g., white to yellow, and then after some substantially predetermined delay, a second color change can indicate that enough time has elapsed to hydrate the hairs for optimum shaving.

EXAMPLE

One example provides a two part reaction in which the shaving preparation initially changes color when applied to a wet face and then after an appropriate amount of time, the shaving preparation changes again to its final color indicating that the beard is prepared for shaving. The initial reaction resulting from the presence of water implements a pH indicator that can include but is not limited to Thymol Blue. The second reaction is based on an oxidation reaction and incorporates a customized leuco dye which when activated changes color at a predetermined rate. These two dyes are incorporated into the shaving gel, by controlling the pH of the gel and by deoxygenating the gel under manufacturing conditions. The preferred indicator requires the gel pH to be maintained around 8.5, which will provide the maximum flexibility in color change for this indicator. For the leuco dye, the gel is substantially deoxygenated because the dye is oxygen sensitive once placed in a basic environment. During manufacturing, oxygen can be removed from the gel components by bubbling each solution with nitrogen and maintaining a nitrogen blanket during processing. The product is then inserted into dispensing units under pressure using standard industry procedures.

Similarly, scents can be emitted from the shaving preparation to provide an indication that the shaving preparation is being applied with water and that enough time has elapsed for the hairs to hydrate and soften. Reactions whose by-products consist of at least one aromatic compound and generate a concentration high enough to be noticeable to the user would be suitable. The rate of such reactions can be adjusted by the use of encapsulates or protective groups on one of the reactants. Aromatic compounds encapsulated would also generate a scent once released. Compound release rates would depend on the rate of capsule degradation. Oxidation, hydration, or acid-base reactions can release the encapsulant. Scents can also be used in conjunction with color indicators. Hydration, oxidative, or acid-base reactions, and reactive encapsulant resulting in scented by-products or scented product release are useful for this application.

According to another embodiment of the present invention, color changes resulting from a physical or physical/chemical change can be implemented. Light diffraction in association with a colloidal array consisting of small polystyrene spheres, which may or may not comprise chemical binding sites, included in a shaving preparation are one method to incorporate a physical color change. The polystyrene spheres are capable of diffracting light and the color of the diffracted light is dependent on the distance between the spheres. As the shaving preparation hydrates, the distance between spheres changes and a color change results. The hydration can cause an increased spacing within the colloidal array via repulsion or attraction. Alternatively, changes in the colloidal array spacing can result from water binding to specified water binding sites on the polystyrene spheres.

Colloidal array technology can also be utilized to provide a color change after a pre-determined amount of time, such as the time that it would be expected for the shaving preparation to properly hydrate and soften the hair. Such color changes utilize the diffusion characteristics of water within the colloidal array. The rate of bonding between the water and the water binding sites, and/or additional binding sites which have a desired bonding rate for water can be implemented to adjust the reaction time to provide a color change as long as required to hydrate and soften the hairs.

These and other hydrochromic reactions can be utilized without departing from the scope of the present invention in order to indicate that conditions exist on the surface being shaved, that the shaving surface has been properly prepared with water and shaving preparation, that a sufficient amount of time has elapsed since the application of the water to the shaving preparation or combinations thereof.

The reactions occurring within shaving preparations of some embodiments of the present invention can also be initiated by some condition that is not present in the container, e.g. can, of the shaving preparation. For example, a timed reaction can be initiated in response to light or a reduction in pressure encountered by the shaving preparation after the shaving preparation has been dispensed from its container. The dispensing unit may also consist of two or more separate compartments that hold the reactants separately while packaged but result in reactant mixing when dispensed.

Shaving preparations typically consist of one or more of the following; fatty acids, bases, surfactants, humectants, lubricants, propellants, foaming agents, and fragrances. Shaving preparations of the present invention that advantageously alert the user when the desired shaving conditions exist preferably incorporate the indicating ingredient or ingredients within the shaving preparation formulation. For oxidation, photochemical, and the like chemistries that react to standard environmental conditions, special procedures may be required to eliminate or isolate the initiator during processing and packaging.

Another aspect of the present invention illustrated in FIG. 1 comprises a shaving preparation in combination with a dispenser. The dispenser 10 comprises a first inner chamber 20 and a second chamber 30 which is isolated from the first chamber 20. According to this embodiment of the present invention, when the dispenser 10 is activated, the components of both chambers are dispensed. A first component 25 from the first chamber 20 mixes with a second component 35 from the second chamber 30 and initiates a chemical reaction resulting in a discernible change to the person shaving. Either of the chambers may only comprise an initiator while the remainder of the shaving preparation can be in the other chamber. According to an alternative embodiment of the present invention which is not illustrated, the second chamber 30 can be selectively activated, for example, by the movement of a selector bar. In this manner, the chemical reaction resulting in the discernible change will only occur when a switch or other selector is set to a desired position. At other times, only the remainder of the shaving preparation is dispensed.

According to an alternative embodiment of the present invention, a shaving preparation comprises a component which undergoes a discernable chemical change when exposed to the atmosphere during shaving. The discernable chemical change can be initiated utilizing various mechanisms. For example, the chemical change could be initiated when the shaving preparation contacts air, upon the change in moisture, or upon a reduction in pressure. For example, those skilled in the art will appreciate that the contents in a shaving preparation dispenser can be maintained under pressure in order to facilitate dispensing by the person shaving.

We claim:

1. A shaving preparation for use in preparing hair for shaving comprising at least one substance which undergoes a discernable chemical change indicating a desired shaving condition exists.

2. A shaving preparation according to claim 1 further comprising at least one compound selected from the group consisting of surfactants, lubricants, humectants, foaming agents, fragrances, fatty acids, bases, and propellants.

3. A shaving preparation according to claim 1 wherein said discernible chemical change is a change in an amount of water in said shaving preparation.

4. A shaving preparation according to claim 1 wherein said desired shaving condition is the hydration of hair.

5. A shaving preparation according to claim 1 wherein said desired shaving condition is the length of time the shaving preparation has been in contact with additional water.

6. A shaving preparation according to claim 1 wherein said desired shaving condition is the length of time the shaving preparation has been in contact with hair or skin.

7. A shaving preparation according to claim 1 wherein said desired shaving condition is the length of time the shaving preparation has been exposed to the atmosphere.

8. A shaving preparation according to claim 1 wherein said desired shaving condition is the amount of additional water in contact with the shaving preparation.

9. A shaving preparation according to claim 1 wherein discernible change comprises a change in color.

10. A shaving preparation according to claim 9 wherein the entire shaving preparation changes color.

11. A shaving preparation according to claim 9 wherein only a portion of said shaving preparation changes color.

12. A shaving preparation according to claim 1 wherein said discernible change comprises a change in diffraction properties of said substance.

13. A shaving preparation according to claim 1 wherein said descernable change comprises a change in temperature.

14. A shaving preparation according to claim 1 wherein said discernible change comprises a change in scent.

15. A shaving preparation according to claim 1 wherein said discernible change comprises a visual change and at least one other discernible change.

16. A shaving preparation according to claim 1 wherein said discernible change comprises a temperature change and at least one other discernible change.

17. A shaving preparation according to claim 1 wherein said discernible change comprises an aromatic change and at least one other discernible change.

18. A shaving preparation according to claim 1 wherein said substance changes color.

19. A shaving preparation according to claim 1 wherein said substance comprises a colloidal array.

20. A shaving preparation according to claim 1 wherein said substance changes temperature.

21. A shaving preparation according to claim 1 wherein said substance emits a scent.

22. A shaving preparation according to claim 1 wherein said substance undergoes oxidation.

23. A shaving preparation according to claim 1 wherein said substance undergoes hydration.

24. A shaving preparation according to claim 1 wherein said substance undergoes an acid-base reaction.

25. A shaving preparation according to claim 1 wherein said substance comprises a leuco dye.

26. A shaving preparation according to claim 1 wherein said substance comprises a colorant.

27. A shaving preparation according to claim 1 wherein said substance comprises a reduced colorant.

28. A shaving preparation according to claim 1 wherein said substance is encapsulated.

29. A shaving preparation according to claim 1 wherein said substance is synthesized with protective groups.

30. A shaving preparation according to claim 1 wherein said substance undergoes an exothermic reaction.

31. A shaving preparation according to claim 1 wherein said substance undergoes an endothermic reaction.

32. A shaving preparation according to claim 1 wherein said substance comprises a zeolite.

33. A shaving preparation in combination with a dispenser comprising:
   a dispenser comprising a first chamber and a second chamber isolated from said first chamber;
   a shaving preparation comprising a first component in said first chamber and a second component in a second chamber, wherein said first component and said second component react resulting in a discernible chemical change when mixed during shaving, said change indicating a desired shaving condition.

34. A shaving preparation in combination with a dispenser according to claim 33 wherein said first component comprises an oxidant.

35. A shaving preparation in combination with a dispenser according to claim 33 wherein said second component comprises reduced colorant.

36. A shaving preparation in combination with a dispenser comprising:
   a dispenser comprising a chamber comprising a shaving preparation;
   a shaving preparation comprising at least one component which undergoes a discernible chemical change when exposed to the atmosphere during shaving, said change indicating desired shaving condition.

37. A shaving preparation in combination with a dispenser according to claim 36 wherein said discernible chemical change occurs upon contact with air.

38. A shaving preparation in combination with a dispenser according to claim 36 wherein said discernible chemical change occurs upon change in moisture.

39. A shaving preparation in combination with a dispenser according to claim 36 wherein said discernible chemical change occurs upon a reduction in pressure.

40. A shaving preparation for use in preparing hair for shaving comprising at least one substance which undergoes a discernible change indicating a desired shaving condition wherein said substance comprises a colloidal array.

41. A shaving preparation according to claim 40 further comprising at least one compound selected from the group consisting of surfactants, lubricants, humectants, foaming agents, fragrances, fatty acids, bases, and propellants.

42. A shaving preparation according to claim 40 wherein said desired shaving condition is the amount of water in said shaving preparation.

43. A shaving preparation for use in preparing hair for shaving comprising at least one discernibly chargeable substance wherein said shaving preparation undergoes a first discernible change indicating a first desired shaving condition and, after a period of time following said first discernible change, a second, distinct discernible change indicating a second desired shaving condition.

44. A shaving preparation according to claim 43 wherein a first substance undergoes said first change and a second substance undergoes said second change.

45. A shaving preparation according to claim 43 wherein said first substance comprises a dye.

46. A shaving preparation according to claim 43 wherein one of said changes comprises a change in scent.

47. A shaving preparation according to claim 43 wherein one of said changes comprises a change in color.

48. A method of preparing hair for shaving comprising the step of applying to an area being shaved at least one substance which undergoes a discernable chemical change indicating a desired shaving condition exists.

49. The method of claim 48 further comprising the step of providing at least one compound selected from the group consisting of surfactants, lubricants, humectants, foaming agents, fragrances, fatty acids, bases and propellants.

50. The method of claim wherein said discernible chemical change is a change in an amount of water in said shaving preparation.

51. The method of claim 48 wherein said desired shaving condition is the hydration of hair.

52. The method of claim 48 wherein said desired shaving condition is a length of time the shaving preparation has been in contact with additional water.

53. The method of claim 48 wherein said desired shaving condition is a length of time the shaving preparation has been in contact with hair or skin.

54. The method of claim 48 wherein said desired shaving condition is a length of time the shaving preparation has been exposed to the atmosphere.

55. The method of claim 48 wherein said desired shaving condition is an amount of additional water in contact with the shaving preparation.

56. The method of claim 48 wherein said discernible chemical change comprises a change in color.

57. The method of claim 56 wherein an entirety of said shaving preparation changes color.

58. The method of claim 56 wherein only a portion of said shaving preparation changes color.

59. The method of claim 48 wherein said discernible chemical change comprises a change in diffraction properties of said substance.

60. The method of claim 48 wherein said discernable chemical change comprises a change in temperature.

61. The method of claim 48 wherein said discernible chemical change comprises a change in scent.

62. The method of claim wherein said discernible chemical change comprises a visual change and at least one other discernible chemical change.

63. The method of claim 48 wherein said discernible chemical change comprises a temperature change and at least one other discernible chemical change.

64. The method of claim 48 wherein said discernible chemical change comprises an aromatic change and at least one other discernible chemical change.

65. The method of claim 48 wherein said at least one substance changes color.

66. The method of claim 48 wherein said at least one substance comprises a colloidal array.

67. The method of claim 48 wherein said at least one substance changes temperature.

68. The method of claim 48 wherein said at least one substance emits a scent.

69. The method of claim 48 wherein said at least one substance undergoes oxidation.

70. The method of claim 48 wherein said at least one substance undergoes hydration.

71. The method of claim 48 wherein said at least one substance undergoes an acid-base reaction.

72. The method of claim 48 wherein said at least one substance comprises a leuco dye.

73. The method of claim 48 wherein said at least one substance comprises a colorant.

74. The method of claim 48 wherein said at least one substance comprises a reduced colorant.

75. The method of claim 48 wherein said at least one substance is encapsulated.

76. The method of claim 48 wherein said at least one substance is synthesized with protective groups.

77. The method of claim 48 wherein said at least one substance undergoes an exothermic reaction.

78. The method of claim 48 wherein said at least one substance undergoes an endothermic reaction.

79. The method of claim 48 wherein said at least one substance comprises a zeolite.

* * * * *